United States Patent
Lovewell

(10) Patent No.: US 6,730,079 B2
(45) Date of Patent: May 4, 2004

(54) METHOD FOR CALCULATING IMPEDANCE AND APPARATUS UTILIZING SAME

(75) Inventor: James G. Lovewell, San Leandro, CA (US)

(73) Assignee: Medtronic Vidamed, Inc., Minneapolis, MN (US)

(*) Notice: Subject to any disclaimer, the term of this patent is extended or adjusted under 35 U.S.C. 154(b) by 169 days.

(21) Appl. No.: 10/201,401

(22) Filed: Jul. 22, 2002

(65) Prior Publication Data

US 2004/0015160 A1 Jan. 22, 2004

(51) Int. Cl.$^7$ ............................................. A61B 18/18
(52) U.S. Cl. ................................................ 606/34; 606/38
(58) Field of Search ........................ 606/32–34, 37–42; 128/898

(56) References Cited

U.S. PATENT DOCUMENTS

| | | | |
|---|---|---|---|
| 5,370,675 A | 12/1994 | Edwards et al. ............ 607/101 |
| 5,385,544 A | 1/1995 | Edwards et al. ............ 604/22 |
| 5,549,644 A | 8/1996 | Lundquist et al. ............ 604/22 |
| 5,964,756 A | 10/1999 | McGaffigan et al. ............ 606/41 |
| 6,228,080 B1 * | 5/2001 | Gines ............ 606/34 |
| 6,238,387 B1 * | 5/2001 | Miller, III ............ 606/34 |
| 6,391,024 B1 * | 5/2002 | Sun et al. ............ 606/34 |
| 6,638,275 B1 | 10/2003 | McGaffigan et al. ............ 606/41 |
| 2004/0015161 A1 * | 1/2004 | Lovewell ............ 606/34 |

* cited by examiner

Primary Examiner—Michael Peffley
(74) Attorney, Agent, or Firm—IPLM Group, P.A.

(57) ABSTRACT

A method for calculating the impedance in a first circuit coupling a first radio frequency electrode to a radio frequency controller where the first electrode is disposed in tissue in the vicinity of a second radio frequency electrode coupled to a second circuit. The impedance IMP of the first circuit is measured when energy is being supplied to both electrodes. The impedance $IMP_0$ of the first circuit is also measured when energy is being supplied to the first electrode but not to the second electrode, and subtracted from the impedance value IMP to determine a delta value $IMP_A$. The impedance $IMP^2$ of the first circuit is then measured when energy is being supplied to both electrodes. The impedance delta value $IMP_A$ is subtracted from the impedance value $IMP^2$ to arrive at a calculated impedance value for the first circuit. A computer-readable memory and apparatus utilizing the method are provided.

16 Claims, 5 Drawing Sheets

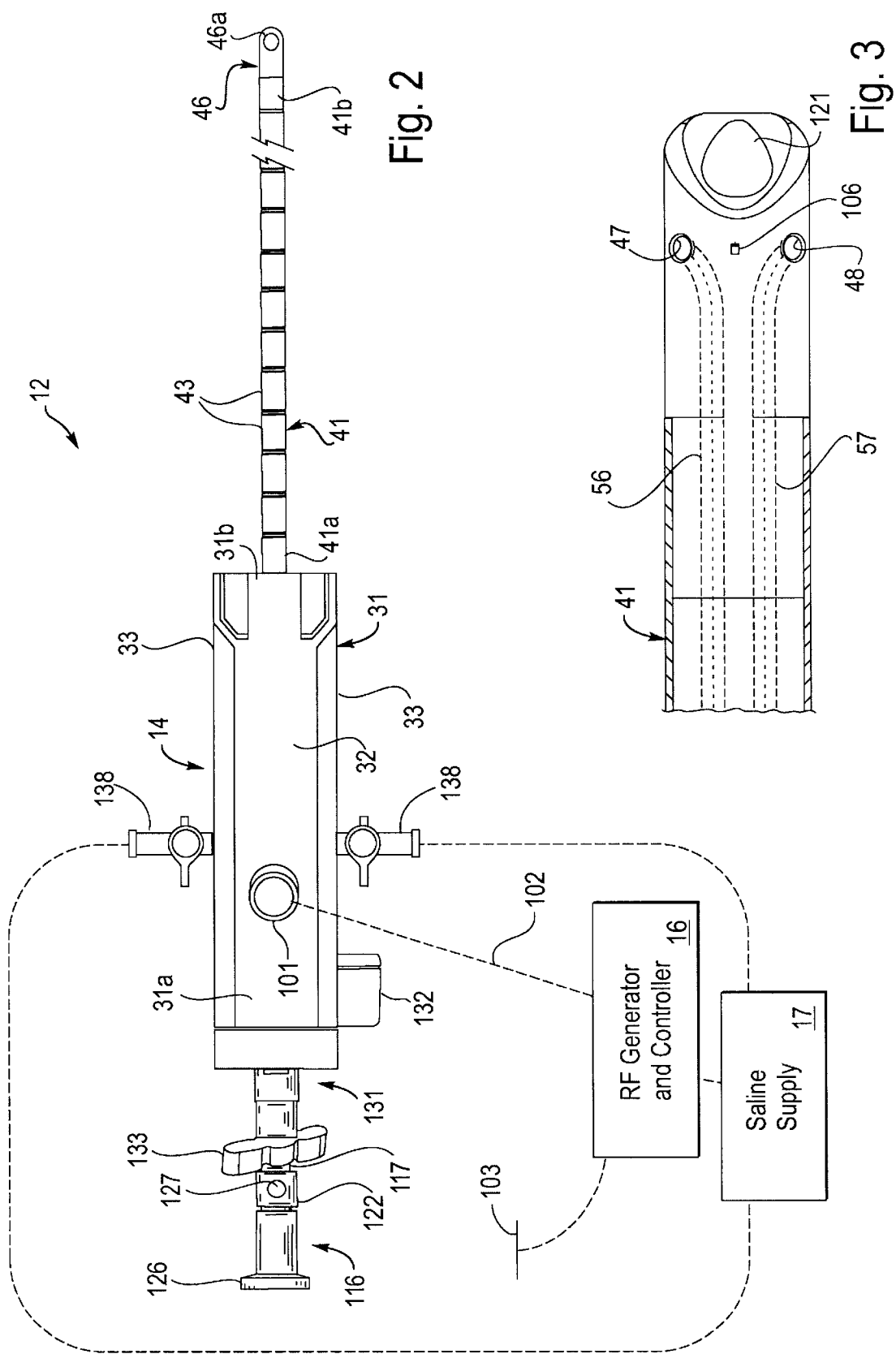

METHOD FOR CALCULATING IMPEDANCE AND APPARATUS UTILIZING SAME

FIELD OF THE INVENTION

This invention pertains generally to methods and apparatus for treating tissue and, more particularly, to methods and apparatus for treating tissue utilizing radio frequency energy.

BACKGROUND

Medical devices have been provided for treating tissue of a mammalian body by the use of radio frequency energy. See, for example, U.S. Pat. Nos. 5,370,675, 5,385,544 and 5,549,644. Radio frequency energy passing from an electrode of such a device through the adjoining tissue causes heating of the tissue. In a monopolar device, the radio frequency energy passes from the active electrode to an indifferent electrode typically in contact with the exterior of the body of the patient. In order to cause desired tissue ablation and subsequent necrosis, the treated tissue is heated to a temperature in excess of approximately 47° C. However, if the temperature of the tissue being treated is elevated too high, dehydration and later charring of the tissue can occur. Such dehydration and charring can increase the impedance of the tissue to a level that prohibits radio frequency from traveling through the tissue. In view of the foregoing, prior systems have monitored the impedance of the active electrode circuit and adjusted the amount of radio frequency energy supplied to the electrode in response to such impedance measurements.

Some previously provided medical devices utilize multiple radio frequency electrodes that can be disposed in the vicinity of each other in the tissue being treated. Where the amount of radio frequency energy being delivered to such electrodes varies, it has been found that crosstalk can occur between the electrodes. In a monopolar device, for example, current may travel from one active electrode down the circuit of the other active electrode to the radio frequency generator. Where the impedance of the active electrode circuit is being monitored, such crosstalk current can result in erroneously high impedance measurements and thus unwanted reductions in radio frequency energy to the active electrode with the high impedance measurement.

It would be desirable to provide a method and apparatus that reduces the contribution of crosstalk between adjacent electrode circuits when monitoring the impedance of the electrode circuits.

SUMMARY OF THE INVENTION

A method is provided for calculating the impedance in a first circuit coupling a first radio frequency electrode to a radio frequency controller where the first radio frequency electrode is disposed in tissue of a mammalian body in the vicinity of a second radio frequency electrode coupled to a second circuit distinct from the first circuit. In the method, the impedance of the first circuit is measured to determine an impedance value IMP when radio frequency energy is being supplied to the first and second radio frequency electrodes. The impedance of the first circuit is also measured to determine an impedance value $IMP_0$ when radio frequency energy is being supplied to the first radio frequency electrode but not to the second radio frequency electrode. The impedance value $IMP_0$ is subtracted from the impedance value IMP to determine an impedance delta value $IMP_A$. The impedance of the first circuit is remeasured to determine an impedance value $IMP^2$ when radio frequency energy is being supplied to the first and second radio frequency electrodes. The impedance delta value $IMP_A$ is subtracted from the impedance value $IMP^2$ to arrive at a calculated impedance value for the first circuit. A computer-readable memory and apparatus utilizing the method are provided.

BRIEF DESCRIPTION OF THE DRAWINGS

FIG. 2 is a top elevational view of the apparatus and system of FIG. 1 taken along the line 2—2 of FIG. 1.

FIG. 3 is a bottom elevation view of a portion of the apparatus of FIG. 1 taken along the line 3—3 of FIG. 1.

DESCRIPTION OF THE INVENTION

Figure 1:
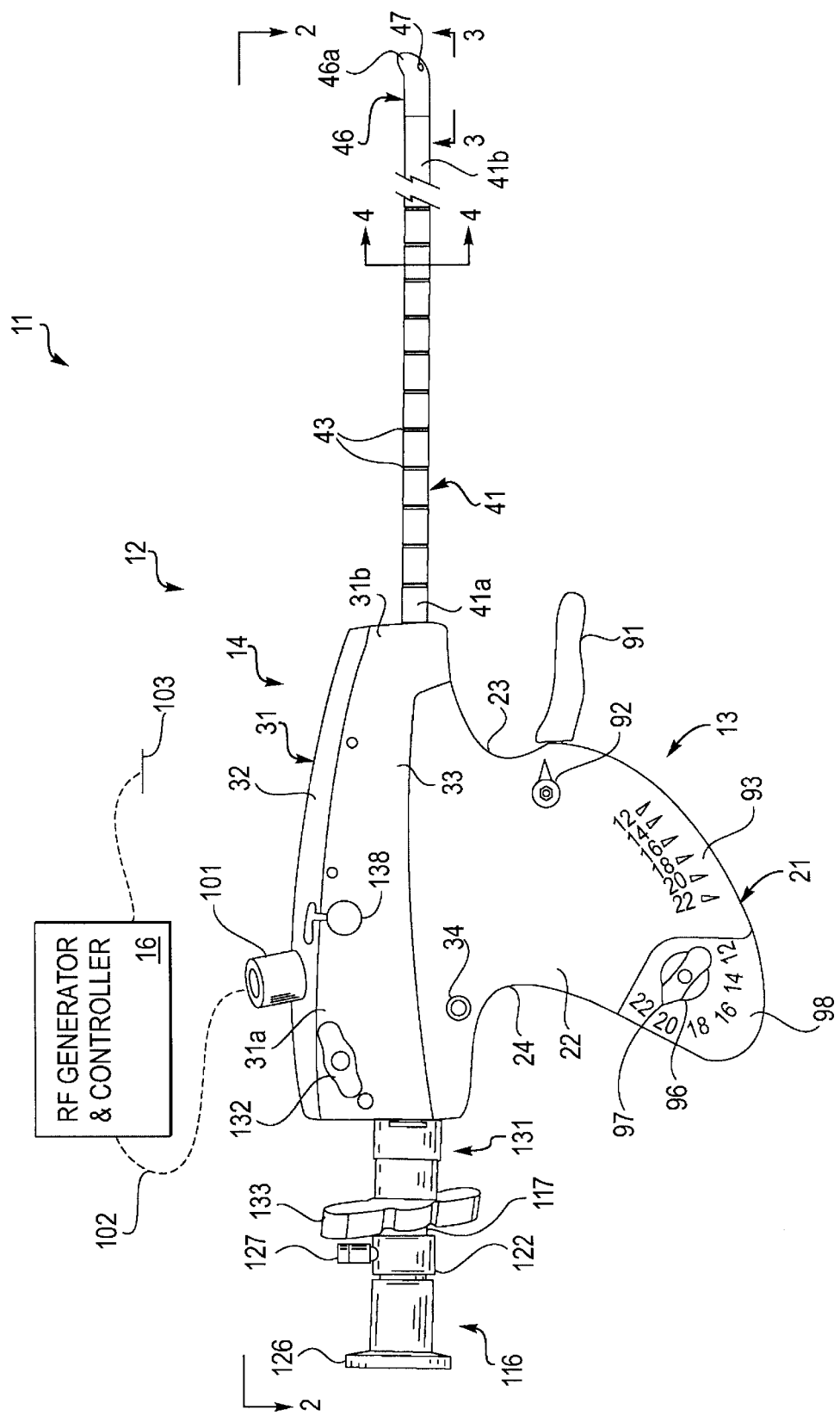
FIG. 1 is a side elevational view of an apparatus and system utilizing the method for calculating impedance of the present invention.

The method and apparatus of the present invention are for treating a mammalian body, such as a human patient. Such apparatus is part of a system 11 and can be in the form of a transurethral needle ablation apparatus or device 12 similar to the apparatus shown in U.S. Pat. No. 5,964,756 and in U.S. patent application Ser. No. 09/684,376 filed Oct. 5, 2000, the entire content of each of which is incorporated herein by this reference. Device 12 includes a reusable handle 13 on which there is mounted a detachable cartridge 14. The needle electrodes of the device are supplied with radio frequency energy from a radio frequency generator and controller 16, which can be similar to the type commercially available from Medtronic, Inc. of Minneapolis, Minn. The device 12 is further supplied with a conductive liquid such as a saline solution provided from one or more reservoirs and preferably from a saline supply 17 (see FIG. 2). Controller 16 is preferably coupled to the saline supply 17 to control the output thereof. The method and apparatus of the present invention can be utilized to calculate the impedance in the electrode circuits providing radio frequency energy to the needle electrodes of the apparatus.

Apparatus 12 is similar in construction to the apparatus disclosed in U.S. Pat. No. 5,964,756. Using that same construction, handle 13 is comprised of a housing 21 which is ergonomically shaped so as to be adapted to fit in a human hand. Specifically, the handle 13 is in the form of a pistol grip which has a main body portion 22 that is provided with a forward indentation 23 adapted to receive the index finger of the human hand grasping the handle 13 and a larger rearwardly facing indentation 24 adapted to receive the thumb of the same human hand. Housing 21 is made from metal or any other suitable material.

Cartridge 14 consists of a cover 31 that is generally U-shaped in cross section and is formed of a suitable material such as plastic. The cover 31 is provided with proximal and distal extremities 31a and 31b and is formed by a curved top wall 32 and depending adjoining spaced-apart parallel side walls 33. A release button 34 is provided on each of the opposite sides of the housing 21 for releasing the removable cartridge 14 from the handle 13.

An elongate tubular member or probe 41 preferably in the form of a rigid torque tube made from any suitable material such as stainless steel is provided and includes proximal and distal extremities 41a and 41b. Probe 41 has its proximal extremity mounted to the distal extremity 31b of cover 31. The tubular torque member 41 has a suitable diameter as for example 18.5 French and is provided with a passage 42 circular in cross section extending therethrough (see FIG. 3). The outer surface of the probe 41 is provided with spaced-apart markings 43 which are spaced apart by one centimeter increments to aid the physician in insertion of the probe 41 into the urethra.

A bullet-shaped tip or distal guide housing 46 formed of a suitable plastic transparent to light is secured to the distal extremity of the torque tube or probe 41 in the manner described in U.S. Pat. No. 5,964,756 (see FIGS. 1 and 3). As shown in FIG. 1, the distal tip 46 has an upturned rounded portion 46a. The elongate probe 41 and the tip 46 preferably have a combined length of approximately 9.5 inches. A pair of circumferentially spaced-apart holes 47 and 48 are provided on the underside of the bullet-shaped tip 46 opposite the upturned portion 46a. The first and second holes 47 and 48 are spaced apart from each other by a suitable distance as for example one centimeter, which dimension is determined by the diameter of the torque tube 46 (see FIG. 3). First and second angled guide tubes 51 and 52 which are aligned with the respective first and second holes 47 and 48 have L-shaped 90° bends therein that are molded into the transparent bullet-shaped tip 46. Such 90° bends provided in the first and second angled guide tubes provide transitions from movement through the tubes along a longitudinal axis to movement along a transverse axis extending at 90° with respect to the longitudinal axis.

Figure 4:
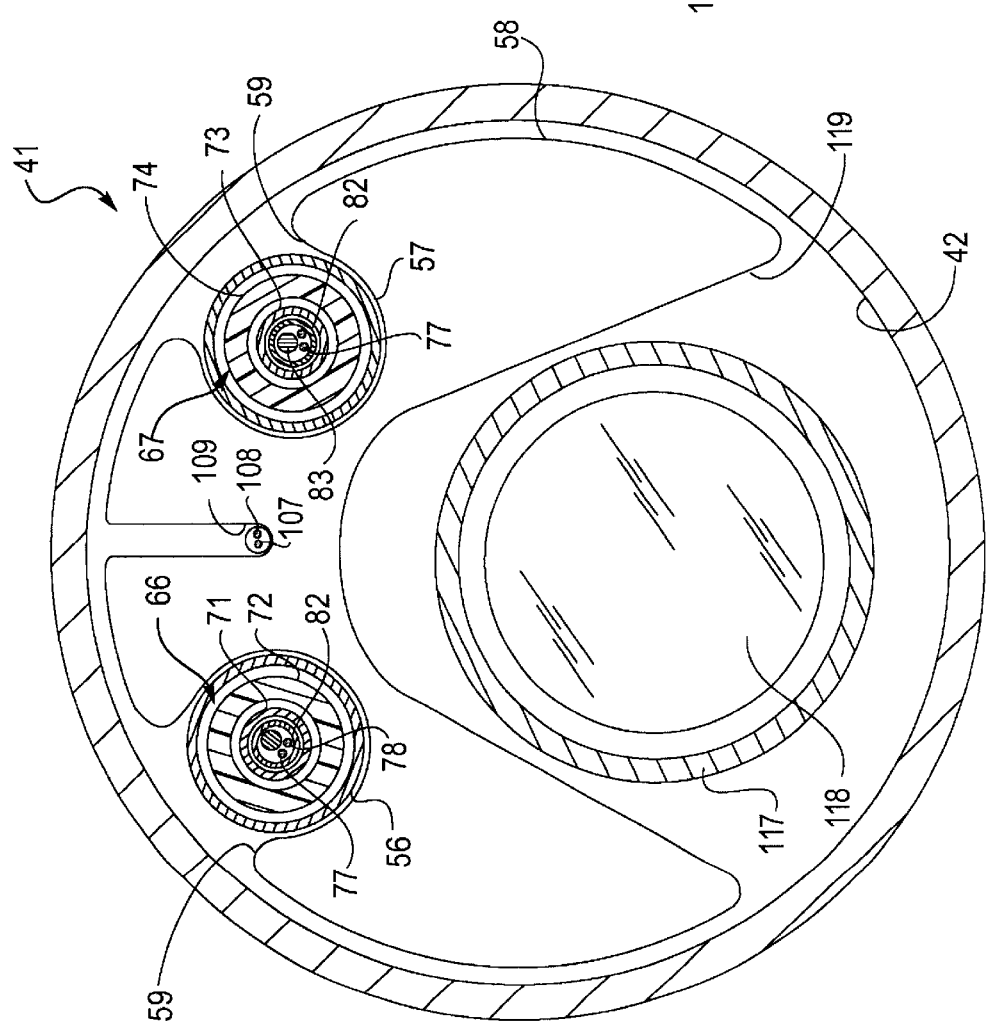
FIG. 4 is a cross-sectional view of the apparatus of FIG. 1 taken along the line 4—4 of FIG. 1.

The first and second angled guide tubes 51 and 52 adjoin straight guide tubes 56 and 57, respectively, which extend through the passage 42 provided in the torque tube or elongate probe 41 (see FIGS. 3 and 4). Each of the straight guide tubes 56 and 57 has a proximal extremity attached to cover 31 and a distal extremity attached to the distal tip 46. As shown particularly in FIG. 4, the straight guide tubes 56 and 57 are supported in predetermined spaced-apart positions in the passage 42 by an insert 58 formed of plastic that is disposed in the torque tube 41 and has spaced-apart recesses 59 formed in the outer periphery of the insert 58. The straight guide tubes 56 and 57 are made from plastic or any other suitable material.

Figure 5:
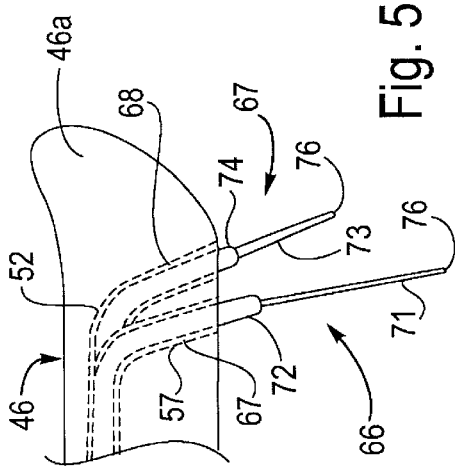
FIG. 5 is an enlarged view of the distal extremity of the apparatus of FIG. 1 wherein the first and second stylets of the apparatus are partially deployed.
Figure 6:
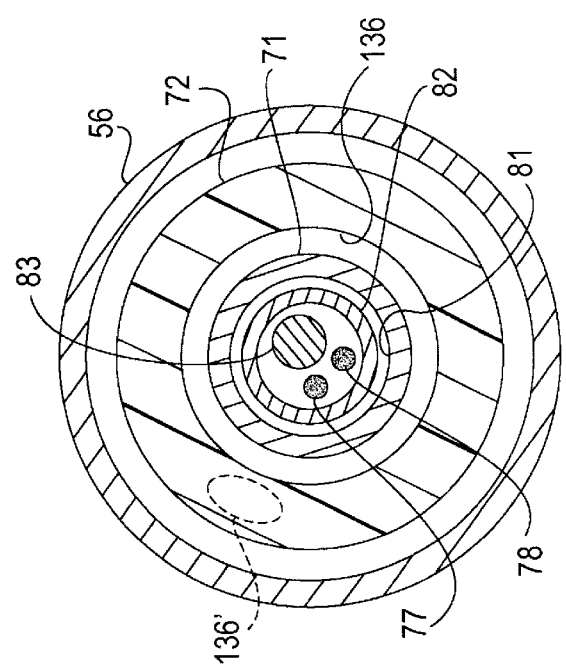
FIG. 6 is an enlarged cross-sectional view of a portion of the apparatus shown in FIG. 4.

A pair of first and second elongate members or stylets 66 and 67 are slidably mounted in the first and second straight guide tubes 56 and 57 within probe 41 (see FIGS. 4–6). Each of the elongate stylets has a proximal extremity, not shown, disposed in cover 31 and a distal extremity 68 disposed in the distal extremity of probe 41 and tip 46. First stylet 66 is preferably formed from a needle electrode 71 and a layer of insulating material disposed around the needle electrode but exposing a distal portion of the needle electrode. The layer of insulating material is preferably a sleeve 72 slidably mounted on the needle electrode 71. Second stylet 67 is similar in construction to the first stylet 66 and includes a needle electrode 73 and a sleeve 74 slidably mounted on the needle electrode 73. The needle electrodes 71 and 73 are preferably formed of a hollow superelastic nickel-titanium material having an outside diameter of 0.018 inch and an inside diameter of 0.012 inch and a wall thickness of 0.003 inch. The sleeves 72 and 74 are preferably made from plastic or any other suitable insulating material and extend through the guide tubes 51, 52, 56 and 57 so that the entire lengths of the needle electrodes 71 and 73 extending through the passage 42 are insulated from each other and from the torque tube 41. The sheaths or sleeves 72 and 74 additionally provide stiffness to the needle electrodes during penetration of the urethral or other passage wall into which tip 46 is introduced. The insulating sheaths are sized in length so that when the needle electrodes are retracted within the bullet-shaped tip 46, they are substantially covered with the insulation. When the needle electrodes are deployed, the sheaths 72 and 74 continue to cover the needle electrodes, but permit the distal portion of the needle electrodes to be exposed in the targeted tissue. The stylets 66 and 67 have an included angle of approximately 40°.

A suitable temperature sensor is optionally carried by each of the first and second stylets 66 and 67. The distal extremity of each of the needle electrodes is provided with a sharpened tip and has a thermocouple 76 or other suitable temperature sensor mounted within the sharpened tip (see FIG. 5). Each thermocouple is provided with a pair of wires 77 and 78 which extend proximally from the sharpened tip through a longitudinal lumen 81 provided in the hollow needle electrode 71 or 73 (see FIGS. 4 and 6). A separate insulating sleeve 82 is provided in each electrode lumen 81 to provide additional insulation isolating the thermocouple wires from the metal needle electrode. In order to strengthen the needle electrodes 71 and 73 and to inhibit wall collapse and kinking during bending, a nickel-titanium rod 83 is disposed within each internal sleeve 82 alongside the thermocouple wires 77 and 78. Strengthening rod 83 has an external diameter of 0.006 inch and each of the thermocouple wires 77 and 78 has an outside diameter of 0.005 inch. The rod 83 and the thermocouple wires 77 and 78 are cemented in place by a suitable polyurethane adhesive (not shown).

Handle 13 and cartridge 14 are provided with internal mechanisms much the same as described in U.S. Pat. No. 5,954,756, wherein the operation of such mechanisms are described in detail. In general, such mechanisms are adapted to be operated by a needle and sheath deployment and retraction trigger 91 that is adapted to be engaged by the forefinger of the hand holding the body portion of the housing 21 (see FIG. 1). The trigger 91 is adapted to be moved from a "load" position indicated by the arrow 92 through a plurality of deployed positions indicated by indicia 93 ranging from 12 to 22 millimeters provided on opposite sides of the housing 21. In this regard, actuation of the trigger 91 initially causes the first and second stylets 66 and 67 to slidably deploy from respective guide tubes 51 and 56 and 52 and 57 so as to extend sidewise in unison from the distal tip. Further downward movement of the trigger 91 causes the insulating sleeves 72 and 74 to retract a predetermined amount relative to the respective needle electrodes 71 and 73. The length of the resulting tissue penetration of stylets 66 and 67 is determined by the position of an interconnected pair of knobs 96, which set stops for limiting movement of the trigger 91 so that overtravel beyond the setting provided by the knobs 96 cannot occur. The interconnected knobs 96 are provided on opposite sides of the housing 21 adjacent the lower extremity of the body 21 and have pointers 97 movable over indicia 98 ranging from 12 to 22 millimeters in the same increments as the indicia 93. The indicia 98 indicate the length of penetration of the needle electrodes 71 and 73, for example through the urethral wall and into the prostatic tissue of the prostate. Sleeves or sheaths 72 and 74 are retracted a predetermined amount as for example six millimeters relative to the needle electrodes so that there is exposed approximately six millimeters of the needle electrodes in the targeted tissue with the insulating sheaths still extending through the urethral or other passage wall so as to protect such wall during RF ablation of the targeted tissue.

Generator and controller 16 is electrically coupled to the first and second stylets 66 and 67, and specifically to the first and second needle electrodes 71 and 73. In this regard, an electrical connector 101 is provided on cover 31 for permitting electrical communication between the generator 16 and the proximal extremity of the needle electrodes. Controller 16 is electrically coupled to connector 101 by means of a cable 102 or other suitable lead. The generator 16 is provided with two channels of radio frequency energy, making it possible to deliver different amounts of power to two or more different needle electrodes which are typically operated in a monopolar fashion utilizing a return or dispersive electrode 103 which can be adhered to exterior of the body of the patient, for example the small of the back of the patient. The proximal ends of first and second thermocouple wires 77 and 78 are also electrically coupled to connector 101 for permitting controller 16 to monitor temperatures sensed thereby.

An optional temperature sensor such as a thermocouple 106 is preferably encapsulated in the bullet-shaped tip 46 and, as shown in FIG. 3, is disposed in the vicinity of stylet openings 47 and 48 provided in the tip. Thermocouple 106, which permits the sensing of urethral wall temperatures, is connected to wires 107 and 108 extending through the passage 42 and is supported in a recess 109 in the insert 58 (see FIG. 4). The wires 107 and 108 are electrically connected within cover 31 to connector 101 for permitting the monitoring of the readings obtained thereby by generator and controller 16. The thermocouple 106 is used to ensure that the highest temperature reached in the urethra does not exceed approximately 47° C. Such hottest location is typically found between the needle pairs 71 and 73 and it is for this reason that the thermocouple 106 is so located.

The cover 31 and the torque tube 41 are preferably sized to receive an optional telescope or scope 116 of a conventional type which includes a tubular member 117 having a rod lens 118 and fiber optics (not shown) surrounding the rod lens (see FIGS. 1 and 2). The scope 116 is movable through the cover 31 and a recess 119 provided in the insert 58 disposed in the passage 72 of the tube 41 and thence into a bore 121 provided in the bullet-shaped tip 46 (see FIG. 3). The bore 121 is in alignment with the recess 119 provided in the torque tube 41. When the distal extremity of the tubular member 117 is positioned within the bore 121, it is possible to view the surrounding region through the transparent tip 46 because the tip 46 has an index of refraction which is similar to the surrounding liquid, such as saline solution, within the urethra or other body passage into which probe 41 has been placed. A fitting 122 is provided on the proximal extremity of the tubular member 117 and includes an eyepiece 126 and a connector 127 for making connection to a fiber optic light source (not shown).

In order to permit movement of the scope 116 into position so that the physician can also observe independently deployment of the first and second needle electrodes 71 and 73, optional means is preferably provided for causing longitudinal movement of the scope 116 relative to the torque tube 41 (see FIGS. 1 and 2). To this end telescope moving means 131, described in detail in copending patent application Ser. No. 09/684,376 filed Oct. 5, 2000 is provided in the proximal extremity 31a of cover 31. In general, the telescope moving means 131 includes a telescope positioning knob 132 extending from one of the side walls 33 of cover 31 and a scope locking lever 133. Release button 34, and the internal mechanisms and operation thereof, are also described in copending patent application Ser. No. 09/684,376 filed Oct. 5, 2000.

Each of the first and second stylets 66 and 67 optionally has a lumen extending from the proximal extremity to the distal extremity of the stylet for permitting a conductive or other fluid to be introduced by apparatus 12 into the tissue being treated. The lumen can be provided in any portion of the stylet and can be in the form of a lumen extending through the needle electrode or through the insulating sleeve. In one preferred embodiment, and as shown in the drawings, each of the insulating sleeves 72 and 74 is provided with a lumen 136 extending longitudinally therethrough. As shown in FIG. 6, the lumen can be an annular lumen 136 extending around the respective needle electrode and permitted by sizing the internal diameter of the insulating sleeve larger than the external diameter of the needle electrode. Alternatively, or in addition, the lumen can be in the form of one or more lumens 136', one of which is shown in dashed lines in FIG. 6, which are offset from the central lumen of the sleeve 72. Where more than one lumen 136' is provided, such lumens can be spaced circumferentially or otherwise about the insulating sleeve.

The lumen 136 is accessible from the proximal extremity of the respective stylet and a reservoir 17 of a suitable conductive liquid such as saline is coupled to the proximal extremity of each stylet for supplying such liquid to the tissue targeted by apparatus 12 (see FIG. 2). One or more suitable fluid connectors 138 are provided on apparatus 12 for permitting fluid communication between reservoir or saline supply 17 and sleeve lumens 136. In the illustrated embodiment of the invention, first and second fluid connectors in the form of first and second stopcocks 138 extend from the opposite side walls 33 of the cover 31 and connect to saline supply 17 by means of suitable lines or tubing, shown in dashed lines in FIG. 2.

Figure 7:
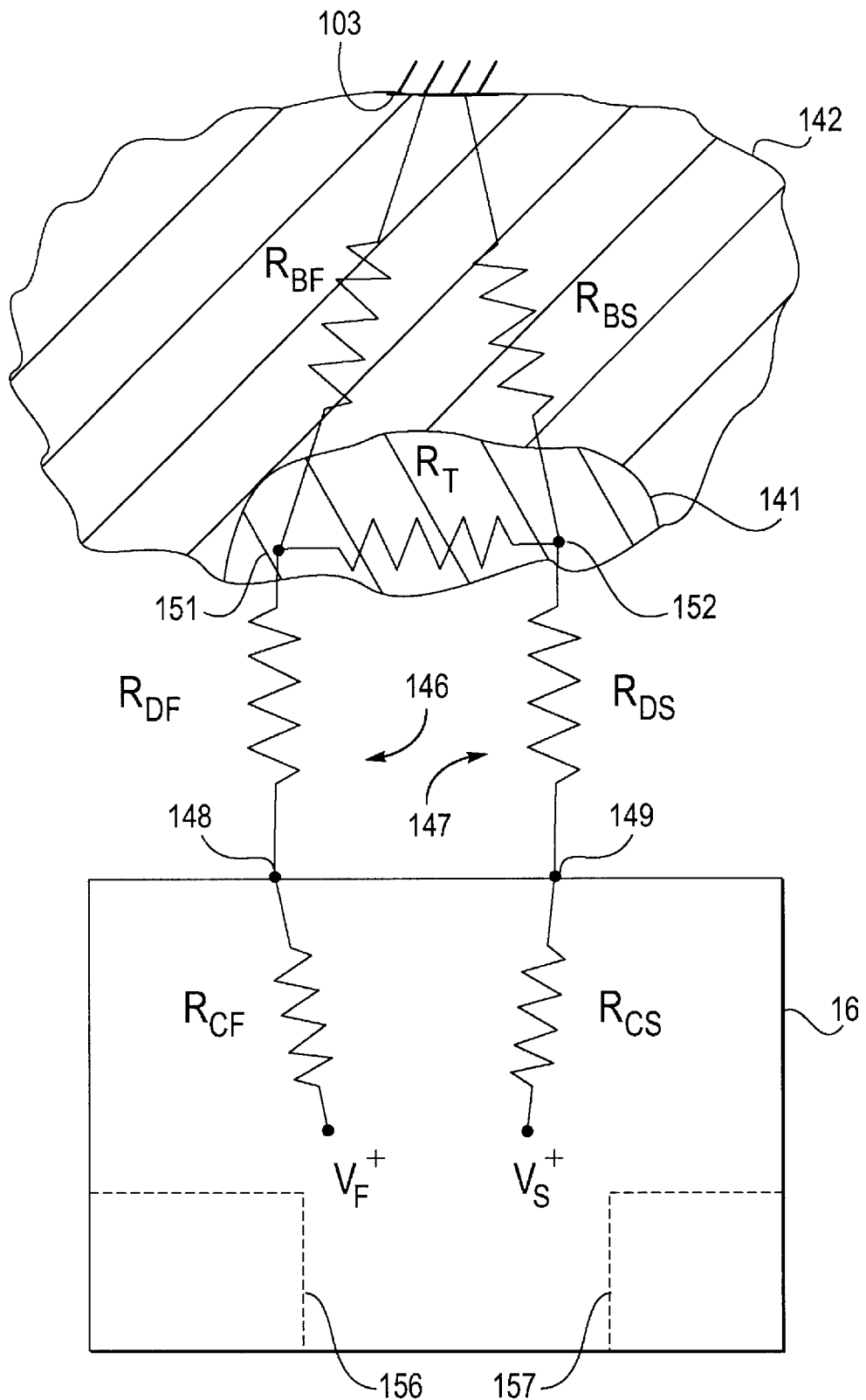
FIG. 7 is a circuit diagram of the radio frequency electrodes of the apparatus of FIG. 1 when disposed adjacent to each other in tissue being treated.

A circuit diagram of system 11 when first and second stylets 66 and 67 are exposed in tissue targeted for treatment is shown in FIG. 7, where targeted tissue 141 of a mammalian body 142 are also depicted. In general, first circuit 146 therein depicts the electrical circuit created by controller 16, cable 102, apparatus 12 and body 142 of the patient pertaining to first stylet 66 and extending from the voltage source $V_F^+$ for such stylet 66 within controller 16 to the return or indifferent electrode 103 preferably adhered to the back side of the patient. Similarly, second circuit 147 depicts the electrical circuit created by controller 16, cable 102, apparatus 12 and body 142 pertaining to second stylet 67 and extending from the voltage source $V_S^+$ to the disbursive electrode 103. Second circuit 147 is distinct from first circuit 146 in that there is no physical connection between such circuits. Nodes 148 and 149 respectively refer to the locations where first and second circuits 146 and 147 connect through cable 102 to controller 16. Nodes 151 and 152 respectively refer to the exposed portions of first and second needle electrodes 71 and 73 within the targeted tissue 141.

The impedance for first circuit 146 within controller 16 is depicted by reference $R_{CF}$ in FIG. 7. The impedance between node 148 and node 151 is depicted by reference $R_{DF}$ and the impedance of body 142, that is between node 151 and return electrode 103, is depicted by reference $R_{BF}$. Similarly, second circuit 147 has respective impedance components $R_{CS}$, $R_{DS}$, and $R_{BS}$. When a current flows between first and second needle electrodes 71 and 73, an impedance exists between nodes 151 and 152 and is depicted in FIG. 7 by reference $R_T$.

Controller 16 includes a central processing unit or central processor 156 and a computer memory 157 electrically coupled to such central processor or CPU 156. Computer-readable memory 157 includes a program for performing the method of the present invention, which is set forth in the flow chart of FIG. 8 and described below.

In one method for treating tissue of the present invention, system 11 can be used to treat benign prostatic hyperplasia in a human male prostate. In such a procedure, the targeted tissue 141 is the prostatic tissue of a prostate. A suitable procedure for treating a prostate of a human male is described in detail in U.S. Pat. Nos. 5,549,644 and 5,964,756, the entire contents of which are incorporated herein by this reference. In general, the distal extremity of torque tube 41 of apparatus 12 is introduced through the penis into the urethra until distal tip 46 is in the vicinity of the prostate. The operating physician then pulls down on trigger 91 to cause the first and second stylets 66 and 67 to deploy from distal tip 46. The sharpened tips of first and second needle electrodes 71 and 73 penetrate the urethral wall to permit the stylets to extend into the prostatic tissue 141 to be treated. As discussed above, further downward movement of trigger 91 causes first and second sleeves 72 and 74 to retract relative to the electrodes. The sleeves, however, extend through the urethral wall so as to protect the wall from radio frequency energy supplied to the needle electrodes 71 and 73.

If the operating physician desires to create a wet electrode within the prostatic tissue 141, a procedure such as described in copending U.S. patent application Ser. No. 10/201,502 filed Jul. 22, 2002, the entire content of which is incorporated herein by this reference, can be utilized. In general, a conductive liquid provided by supply 17 is introduced through first and second stylets 66 and 67 into the prostatic tissue 141 to form such a wet electrode about each of the first and second stylets 66 and 67. The exterior surface of each such wet electrode serves as an outer electrode surface from which radio frequency energy is delivered.

Radio frequency energy is supplied from radio frequency generator and controller 16 to first and second needle electrodes 71 and 73 to create lesions in the prostatic tissue 141 by ablating the tissue. During the application of such energy, the impedance in each of first and second circuits 146 and 147 is monitored to ensure that the impedance $R_{BF}$ in first circuit 146 and the impedance $R_{BS}$ in second circuit 147 are not rising to undesirably high levels so as to thereby inhibit further radio frequency energy from traveling between the stylets 66 and 67 and indifferent electrode 103. In one embodiment, the impedance level in each of first and second circuits 146 and 147 is displayed on a meter or other visual display on controller 16 and, if undesirably high impedance levels are displayed, the operator lowers the radio frequency power supplied to the circuit 146 or 147 having the high impedance level. The temperature sensed by the thermocouple 76 in each of first and second needle electrodes 71 and 73 can also be displayed on the controller so that when undesirably high temperatures appear in one of the electrodes, the operator reduces the radio frequency power supplied to such electrode so as not to cause undesirable dehydration or charring and thus high impedance levels in the vicinity of the electrode.

Controller 16 can further include programs within memory 157 or be otherwise programmed to automatically reduce the amount of radio frequency energy supplied to a needle electrode 71 or 73 in response to an undesirably high impedance or temperature corresponding to such needle electrode. In one preferred embodiment, the aggregate impedance $IMP_F$ in first circuit 146, that is the aggregate of impedances $R_{BF}$, $R_{DF}$ and $R_{CF}$, is monitored 50 times per second for the purpose of controlling the voltage $V_F^-$ being supplied by radio frequency generator and controller 16 to first needle electrode 71 and thus first circuit 146. The aggregate impedance $IMP_S$ in second circuit 147 is similarly monitored in such embodiment.

Figure 8:
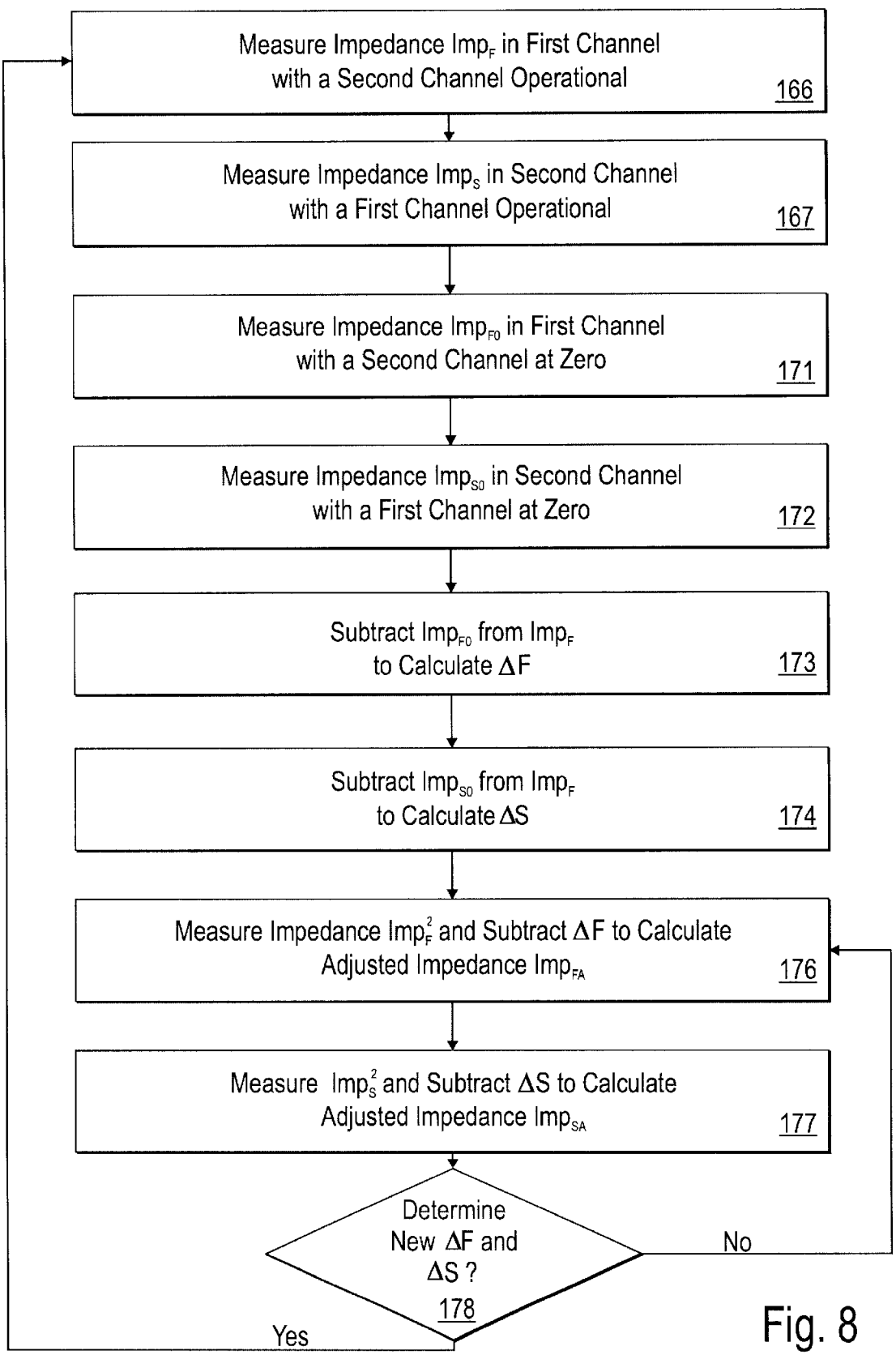
FIG. 8 is a flow chart of the method for calculating impedance of the present invention.

In order to insure that impedance $IMP_F$ in the first circuit or channel 146 is not being undesirably reduced by current traveling from node 152 of second circuit 147 to node 151 of first circuit 146 and back down the circuit 146 to node 148 and controller 16, or similarly that the aggregate impedance $IMP_S$ of second circuit 147 is not being undesirably affected by crosstalk from first circuit 146, controller 16 periodically performs the method set forth in FIG. 8. In one preferred embodiment, the method of FIG. 8 is contained in a computer program stored in memory 157 of the controller 16.

In step 166 of the method of the present invention, controller 16 measures the impedance $IMP_F$ in first channel 146 when radio frequency power is being supplied to each of the first and second channels 146 and 147. In one preferred embodiment, for example, the current traveling through first circuit or channel 146 is measured and then divided into the voltage $V_F^+$ being suppled to the circuit 146 by controller 16 to arrive at impedance $IMP_F$ for the first circuit 146. In step 167, the aggregate impedance $IMP_S$ in second circuit or channel 147 is similarly calculated when radio frequency power is being suppled to each of the first and second circuits 146 and 147.

In step 171 shown in FIG. 8, no radio frequency energy is supplied to second circuit 147 and the impedance $IMP_{FO}$ in first circuit 146 is measured. Since the voltage $V_S^+$ being supplied to the second circuit 147 is zero in step 171, no current travels from the second electrode 73 to the first electrode 71, that is from node 152 to node 151 in FIG. 7, so as to undesirably reduce the aggregate current traveling from controller 16 to indifferent electrode 103 in the first circuit 146 and result in false high impedance readings in such circuit 146. Similarly, and as shown in step 172 in FIG. 8, the impedance $IMP_{SO}$ in second circuit or channel 147 is measured when no voltage and thus no radio frequency energy is being supplied to first circuit 146. In one preferred embodiment, no voltage is supplied to second circuit 147 in step 171 for 29 milliseconds and no voltage is supplied to first circuit 146 in step 172 for 29 milliseconds.

In steps 173 and 174, a delta impedance value is calculated for each of the first and second circuits 146 and 147. In this regard, impedance value $IMP_{FO}$ from step 171 is subtracted from impedance value $IMP_F$ from step 176 to calculate an impedance differential $\Delta F$, also know as an impedance delta value $IMP_A$, in step 173. Similarly, in step 174 impedance value $IMP_{SO}$ from step 172 is subtracted from impedance value $IMP_S$ from step 167 to arrive at an impedance differential $\Delta S$, also know as an impedance delta value $IMP_A$. Steps 173 and 174 can occur while radio frequency energy is being supplied to each of first and second circuits 146 and 147 and the ablation procedure of system 11 is progressing.

In step 176, the aggregate impedance of first circuit 146 is remeasured to determine a remeasured impedance value $IMP_F^2$ when radio frequency energy is being supplied to each of the first and second circuits 146 and 147 and the $\Delta F$ value of step 173 is subtracted from such remeasured impedance value $IMP_F^2$ to calculate an adjusted impedance value $IMP_{FA}$ for the first circuit. Similarly, in step 177 the aggregate impedance for second circuit 147 is remeasured to determine a remeasured impedance value $IMP_S^2$ and $\Delta S$ value from step 174 subtracted therefrom to calculate an adjusted impedance value $IMP_{SA}$ for the second circuit 147. The adjusted impedance values $IMP_{FA}$ and $IMP_{SA}$ are then utilized by the operator and/or controller 16 in the manner discussed above to determine whether any adjustments to the radio frequency energy being supplied to first circuit 146 and or second circuit 147 should be made.

The steps of 176 and 177 can be repeated for a certain number of cycles until the $\Delta F$ and $\Delta S$ values are recalculated, as shown in decision step 178 of FIG. 8. In one preferred embodiment, for example, steps 176 and 177 are repeated until a predetermined event occurs during the procedure which triggers the repetition of steps 166, 167, 171, 172, 173 and 174. Although any one of a number of predetermined events can be utilized in step 178, exemplary predetermined events are an elapse of a certain length of time or a change in the amount of radio frequency energy being supplied to one or both radio frequency electrodes 71 and 73. Thus, for example, when the aggregate impedances of circuit 146 and 147 are being monitored 50 times a second, as discussed above, steps 176 and 177 can be repeated 150 times for a duration of three seconds before controller 16 repeats steps 166, 167, 171, 172, 173 and 174 to determine new $\Delta F$ and $\Delta S$ values. When step 178 determines that new $\Delta F$ and $\Delta S$ values are needed, the procedure shown in FIG. 8 is repeated starting at step 166.

The method and apparatus of the present invention permit greater accuracy in the measurement of the impedance between first radio frequency electrode 71 and the return electrode 103 and in the measurement of the impedance between second radio frequency electrode 73 and the return electrode 103. More accuracy in such impedance measurements permit better control of the size of the lesions created during the procedure, facilitate quicker treatment times and increase the number of successful lesions completed. In this regard, the more accurate impedance readings of the present invention permit higher tissue temperatures to be maintained during the procedure and thus energy to be supplied to the tissue in a shorter period of time.

The foregoing procedure of the invention has been described with the use of first and second stylets 66 and 67, however it should be appreciated that any plurality of stylets can be utilized. Further, it should be appreciated that the apparatus and system of the present invention can be of any suitable type having at least first and second active electrodes. The method can be utilized in any such apparatus and system where the impedance of at least one of the first and second active electrode circuits is monitored and is preferably suited for an apparatus and system utilizing radio frequency energy. Although the method and apparatus of the invention have been described in connection with the treatment of the prostate, such method and apparatus can be used in any tissue of the body.

From the foregoing, it can be seen that a new method and apparatus have been provided for reducing the contribution of crosstalk between adjacent electrode circuits when monitoring the impedance of one or both of the electrode circuits. The method and apparatus permit greater control of lesions created in targeted tissue by adjacent electrodes disposed in the tissue. Radio frequency or any other suitable energy can be supplied to the adjacent electrodes for treating the targeted tissue.

What is claimed is:

1. A method for calculating impedance in a first circuit coupling a first radio frequency electrode to a radio frequency controller where the first radio frequency electrode is disposed in tissue of a mammalian body in the vicinity of a second radio frequency electrode coupled to a second circuit distinct from the first circuit comprising the steps of measuring the impedance of the first circuit to determine an impedance value IMP when radio frequency energy is being supplied to the first and second radio frequency electrodes, measuring the impedance of the first circuit to determine an impedance value $IMP_0$ when radio frequency energy is being supplied to the first radio frequency electrode but not to the second radio frequency electrode, subtracting the impedance value $IMP_0$ from the impedance value IMP to determine an impedance delta value $IMP_\Delta$, remeasuring the impedance of the first circuit to determine an impedance value $IMP^2$ when radio frequency energy is being supplied to the first and second radio frequency electrodes and subtracting the impedance delta value $IMP_\Delta$ from the impedance value $IMP^2$ to arrive at a calculated impedance value for the first circuit.

2. The method of claim 1 wherein the first and second radio frequency electrodes are first and second needle electrodes.

3. The method of claim 2 wherein the first and second needle electrodes are slidably carried by an elongate probe member introduceable into the urethra of a human male for treatment of the tissue of the prostate.

4. The method of claim 2 wherein a temperature sensor is carried by each of the first and second needle electrodes.

5. The method of claim 1 further comprising the step of adjusting the radio frequency energy supplied to the first radio frequency electrode as a function of the calculated impedance.

6. The method of claim 1 wherein the remeasuring and subtracting steps are repeated.

7. The method of claim 6 wherein the remeasuring and subtracting steps are repeated for a predetermined length of time.

8. The method of claim 1 further comprising the step of performing a medical procedure on the tissue.

9. The method of claim 8 wherein the steps of measuring the impedance of the first circuit to determine the impedance value IMP when radio frequency energy is being supplied to the first and second radio frequency electrodes, measuring the impedance of the first circuit to determine the impedance value $IMP_0$ when radio frequency energy is being supplied to the first radio frequency electrode but not to the second radio frequency electrode and subtracting the impedance value $IMP_0$ from the impedance value IMP to determine the impedance delta value $IMP_\Delta$ are repeated after a predetermined event during the procedure.

10. The method of claim 9 wherein the predetermined event is an elapse of a length of time.

11. The method of claim 9 wherein the predetermined event is a change in the radio frequency energy supplied to one of the first and second radio frequency electrodes.

12. The method of claim 1 wherein the second circuit is coupled to the radio frequency controller.

13. A computer-readable memory for use with a radio frequency controller and a first circuit to couple a first radio frequency electrode to the controller and a second radio frequency electrode coupled to a second circuit distinct from the first circuit, the memory containing a computer program for causing the controller to calculate an impedance in the first circuit when the first radio frequency electrode is disposed in tissue of a mammalian body in the vicinity of the second radio frequency electrode by measuring the impedance of the first circuit to determine an impedance value IMP when radio frequency energy is being supplied to the first and second radio frequency electrodes, measuring the impedance of the first circuit to determine an impedance value $IMP_0$ when radio frequency energy is being supplied to the first radio frequency electrode but not to the second radio frequency electrode, subtracting the impedance value $IMP_0$ from the impedance value IMP to determine an impedance delta value $IMP_\Delta$, remeasuring the impedance of the first circuit to determine an impedance value $IMP^2$ when radio frequency energy is being supplied to the first and second radio frequency electrodes and subtracting the impedance delta value $IMP_\Delta$ from the impedance value $IMP^2$ to arrive at a calculated impedance value for the first circuit.

14. The computer-readable memory of claim 13 wherein the computer program further causes the controller to adjust the radio frequency energy being supplied to the first radio frequency electrode as a function of the calculated impedance.

15. A radio frequency controller for use with a first circuit to couple a first radio frequency electrode to the controller and with a second radio frequency electrode coupled to a second circuit distinct from the first circuit comprising a computer-readable memory containing a computer program for causing the controller to calculate an impedance in the first circuit when the first radio frequency electrode is disposed in tissue of a mammalian body in the vicinity of the second radio frequency electrode by measuring the impedance of the first circuit to determine an impedance value IMP when radio frequency energy is supplied to the first and second radio frequency electrodes, measuring the impedance of the first circuit to determine an impedance value $IMP_0$ when radio frequency energy is being supplied to the first radio frequency electrode but not to the second radio frequency electrode, subtracting the impedance value $IMP_0$ from the impedance value IMP to determine an impedance delta value $IMP_\Delta$, remeasuring the impedance of the first circuit to determine an impedance value $IMP^2$ when radio frequency energy is being supplied to the first and second radio frequency electrodes and subtracting the impedance delta value $IMP_\Delta$ from the impedance value $IMP^2$ to arrive at a calculated impedance value for the first circuit, and a central processing unit coupled to the memory for executing the program in the memory.

16. The radio frequency controller of claim 15 wherein the program in the memory further causes the controller to adjust the radio frequency energy being supplied to the first radio frequency electrode as a function of the calculated impedance.

* * * * *